United States Patent
Noire et al.

(10) Patent No.: US 6,864,095 B2
(45) Date of Patent: Mar. 8, 2005

(54) METHOD FOR MAKING AN OPTICAL FIBER CHEMICAL SENSOR COMPRISING A COLORED INDICATOR, USEFUL IN PARTICULAR FOR MEASURING NITRIC ACID

(75) Inventors: Marie-Hélène Noire, Sauveterre (FR); Christophe Bouzon, Odos (FR); Thierry Davin, Lapalud (FR)

(73) Assignees: Commissariat a l'Energie Atomique, Paris (FR); Compagnie Generale des Matieres Nucleaires, Velizy Villacoublay (FR)

( * ) Notice: Subject to any disclaimer, the term of this patent is extended or adjusted under 35 U.S.C. 154(b) by 334 days.

(21) Appl. No.: 10/110,202
(22) PCT Filed: Aug. 21, 2001
(86) PCT No.: PCT/FR01/02639
§ 371 (c)(1), (2), (4) Date: Apr. 17, 2002
(87) PCT Pub. No.: WO02/16914
PCT Pub. Date: Feb. 28, 2002

(65) Prior Publication Data
US 2002/0182740 A1 Dec. 5, 2002

(30) Foreign Application Priority Data
Aug. 22, 2000 (FR) .......................................... 00 10801

(51) Int. Cl.⁷ ............................................. G01N 31/00
(52) U.S. Cl. ..................... 436/72; 436/174; 436/176; 436/106; 422/68.1; 422/82.05; 422/82.06; 422/82.09; 422/83
(58) Field of Search ........................ 436/72, 174, 176, 436/106; 422/68.1, 82.05, 82.06, 82.09, 83

(56) References Cited
FOREIGN PATENT DOCUMENTS

| DE | 197 57 496 | 6/1999 |
|----|------------|--------|
| EP | 0 439 318  | 7/1991 |
| EP | 0 631 127  | 12/1994 |

OTHER PUBLICATIONS

M.H. Noire et al.: "A new sol–gel derived optical fiber sensor for high acidity measurements: application in nuclear fuel reprocessing" Journal of Sol–Gel Science and Technology, vol. 17, pp. 131–136 2000.

*Primary Examiner*—Jill Warden
*Assistant Examiner*—Sam P. Siefke
(74) *Attorney, Agent, or Firm*—Oblon, Spivak, McClelland, Maier & Neustadt, P.C.

(57) ABSTRACT

The invention concerns the production of a chemical sensor which can be used to measure nitric acidity.

This sensor is produced using a sol-gel method for depositing a porous film, containing a colored indicator, on the core of an optic fiber. The pH of the initial sol is adjusted as are other conditions for implementing the sol-gel method to obtain stability of the signal (curves 1 to 4) emitted by the sensor in an 8N nitric medium for at least 1000 hours.

16 Claims, 3 Drawing Sheets

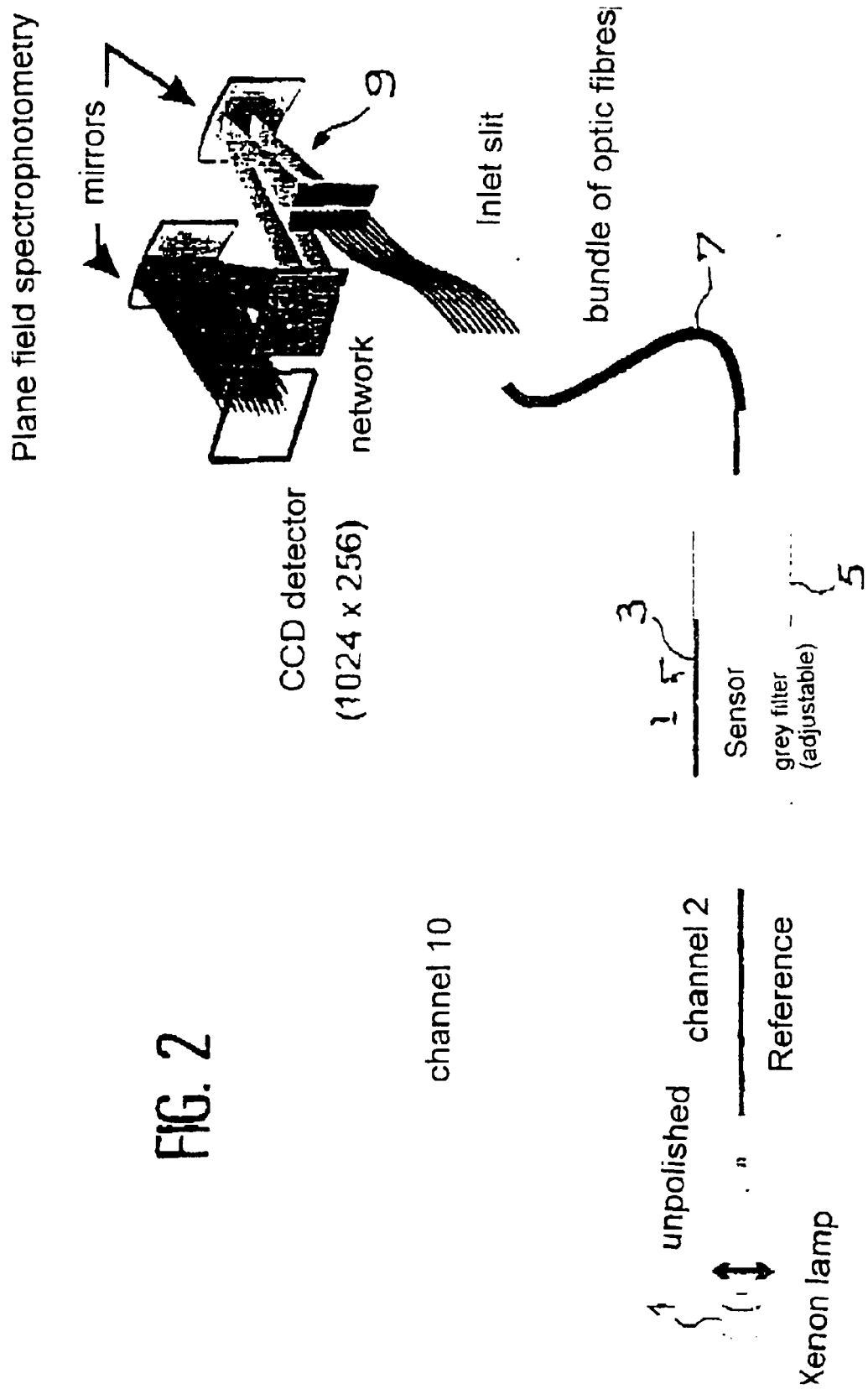

METHOD FOR MAKING AN OPTICAL FIBER CHEMICAL SENSOR COMPRISING A COLORED INDICATOR, USEFUL IN PARTICULAR FOR MEASURING NITRIC ACID

TECHNICAL FIELD

The present invention concerns the production of optic fibre chemical sensors used in particular to measure nitric acidity.

In the area concerning the treatment of spent nuclear fuel, demands in terms of quality and process control require very swift knowledge, even real-time knowledge, of any variations in physical or chemical parameters, in nitric acidity in particular.

During the various steps in the treatment of spent fuel, the on-line measurement of free acidity provides important data which largely contributes to control over extraction methods, to a substantial reduction in waste and to a lighter work load for laboratories.

PRIOR ART

Optic fibre chemical sensors suitable for measuring nitric acidity have been described by M. H. Noiré et al in the following documents:

Sensors and Actuators B51, 1998, pages 214–219 [1], and
Journal of Sol-Gel Science and Technology 17, 2000, pages 131–136 [2].

These sensors measure the absorbency of a coloured indicator sensitive to the protons released by the acid. The coloured indicator, Chromoxane Cyanine R for example, is immobilized on a porous film chemically grafted onto the core of a silica optic fibre. The optic fibre chemical sensor is coupled to a spectrophotometric device for remote, in situ analysis of the acidity. The sensor operates by total mitigated reflection. When this sensor is used, the rays from a light source propagate under multiple reflection in the core of the optic fibre, transiting however along a wave length fraction in the porous film containing the coloured indicator whose colour relates to the acidity of the medium with which it is in contact. The transmitted light, representing the acidity of the medium, is measured by visible UV-spectrophotometry.

The method used for the manufacture of these sensors uses the sol-gel technique, a soft mode chemical technique for the synthesis of metallic oxides. This technique consists of preparing a sol by acid-catalysed hydrolysis of an alcoxysilane-in-alcohol solution containing the coloured indicator, leaving the sol to mature to initiate gelling, followed by its depositing on the core of an optic fibre whose mechanical and optic sheaths have been removed over a central part, and then drying to form a micro-porous film, containing the coloured indicator, grafted onto the core of the fibre.

In this method, the organic precursor, tetraethoxysilane, through hydrolysis and condensation leads to the formation of an inorganic network of low porosity in which the molecules of the coloured indicator are trapped.

To conduct acidity measurement, the optic fibre provided with this porous film is placed in a cell in which the medium to be measured circulates, and which is connected via optic fibres to a multi-channel spectrophotometric system fitted with a CCD detector.

The advantage of such device is the possible simultaneous follow-up of acidity at different points of an installation via several sensors.

The absorbency measured by the detector represents the protonated form of the coloured indicator and is directly linked to the nitric acid concentration of the medium being analysed.

The sensors manufactured to date using this method show analytical performing capacities of interest, but have the disadvantage that they do not have good reproducibility and especially lifetime characteristics owing to desorption of the coloured indicator molecules from the porous film towards the medium to be analysed.

DESCRIPTION OF THE DISCLOSURE

The subject matter of the present invention is precisely a method for manufacturing an optic fibre chemical sensor using the sol-gel technique, which has very high stability, that is to say the capacity to withhold practically the entirety of the coloured indicator in the porous film over very long periods, while allowing the protons released by the acid to diffuse inside this film.

According to the invention, the method of producing a silica-based optic fibre chemical sensor, which can be used to analyse a chemical species present in a liquid or gas, consists of chemically grafting onto the core of the optic fibre a porous film containing a coloured indicator sensitive to the chemical species to be analysed, by conducting the following steps:

a) Preparing a sol by acid-catalysed hydrolysis of a solution of an alcoxysilane in an alcohol, containing the coloured indicator, b) sol maturing c) depositing the sol on the core of the optic fibre, and d) drying and is characterized in that, in step a), the quantity of acid used is such that the pH of the aqueous phase of the sol is 0.44 to 0.72.

In the sol-gel technique, the choice of parameters used is of great importance since these parameters have a direct influence on the final structure of the porous film which is to withhold the coloured indicator.

According to the invention, optimum conditions are chosen to obtain porosity providing total withholding of the coloured indicator while allowing the species to be analysed, for example the protons released by the acid, to diffuse inside the film.

It was therefore found that the pH of the aqueous phase of the sol is a determinant parameter for obtaining the desired microporous characteristics of the grafted film containing the coloured indicator.

The choice of this parameter has an important influence on the gelling time of the sol and on the pore sizes of the dried product subsequently obtained. Hence, with pH values for the aqueous solution of less than 0.72, pores in the microporous region are obtained whereas pH values of more than 0.72 lead to the macroporous domain.

Obtaining a macroporous film is not desirable, since it allows the coloured indicator molecules to diffuse in the solution to be analysed and is detrimental to the reproducibility and lifetime of the sensor.

The pH of the aqueous phase of the sol is generally adjusted to the desired value through the addition of hydrochloric acid. A value of 0.72 relates to a HCl percentage of 2%, 2% meaning 2 moles of HCl per 100 moles of alcoxysilane.

Another important parameter when adjusting the porosity of the grafted film to the desired values concerns sol maturing step b). Preferably, this maturing is conducted at a temperature of 40 to 70° C., preferably between 50 and 60° C., for a period of no more than 3 days.

Indeed, it was verified that maturing time has an influence on the pore size of the dried film. Pore diameter increases with maturing time. Therefore, to limit this diameter, it is appropriate to choose a maturing time which does not exceed 3 days and is preferably between 24 and 50 hours.

A further parameter having a considerable influence on the quality of the porous film is the quantity of water used for hydrolysis during step a) for preparation of the sol. Preferably, a water/alcoxysilane molar ratio of 4 to 6 is used for hydrolysis. By choosing this water/alcoxysilane molar ratio, it is possible to stabilize the density of the film and its porosity characteristics.

In the method of the invention, to carry out step d), vacuum drying is preferred for a time of 20 to 30 hours, preferably for approximately 24 hours. Drying temperature may be 100° C.

According to the invention, the sensor is preferably used after being stored for at least 3 weeks away from light and at room temperature.

This additional storage step also has its importance since it allows for stabilisation of the deposited film. Drying at 100° C., even when conducted on thin films, does not permit total condensation of the alcoxy functions. Therefore the film undergoes change in time through slow condensation of the remaining alcoxy functions. It is therefore most important to use the sensor after this condensation process is completed so as to avoid encountering reproducibility problems for characterization.

Preferably, storage is made for a period ranging from 3 weeks to 2 months. It is also possible to accelerate this condensation process by means of vacuum drying.

The other parameters of this sol-gel manufacturing method have lesser influence on the porosity of the deposited film, and may be chosen from among the values chosen for known production methods of chemical sensors using the sol-gel technique.

Therefore, the alcohol content of the alcoxysilane solution may be such that the alcohol/alcoxysilane molar ratio is approximately 10.

Generally, the alcoxy groups of the alcoxysilane have from 1 to 4 carbon atoms. Preferably tetraethoxysilane is used.

The alcohol used may be an alcohol having from 1 to 4 carbon atoms; preferably ethanol is used which is the most suitable for the synthesis of microporous gels.

In the method of the invention, the coloured indicator is chosen in relation to the chemical species to be analysed by the chemical sensor. If this sensor is intended to measure nitric acidity over the concentration range of 1 to 10 mol/L, the coloured indicator may be Chromoxane Cyanine R or Chromazurol S. Preferably, Chromoxane Cyanine R is used.

If the sensor is intended to measure nitric acidities over a lower concentration range, for example from 0.1 to 2 mol/L, the coloured indicator may be chosen from among Thymol Blue, Phenol Red and Pyrocatechol Violet.

The concentrations of the coloured indicator are chosen such that a sufficient quantity of indicator is obtained in the film. They may be such that the coloured indicator/alcoxysilane molar ratio ranges from $1/300$ to $1/700$. It is preferably 1:335. At higher values, dimers and/or aggregates may occur.

A further subject of the invention is a fibre optic chemical sensor for measuring nitric acidity, obtained using the above method, whose acidity measurement signal is stable for at least 1000 hours in 8 N acid circulated around the porous film.

Other characteristics and advantages of the invention will become better apparent on reading the following description of examples of embodiment given by way of illustration and evidently non-restrictive, with reference to the appended drawings.

SHORT DESCRIPTION OF THE DRAWINGS

FIG. 2 is a diagram illustrating a measurement installation comprising a chemical sensor conforming to the invention.

DETAILED DESCRIPTION OF EMBODIMENTS

Figure 1:
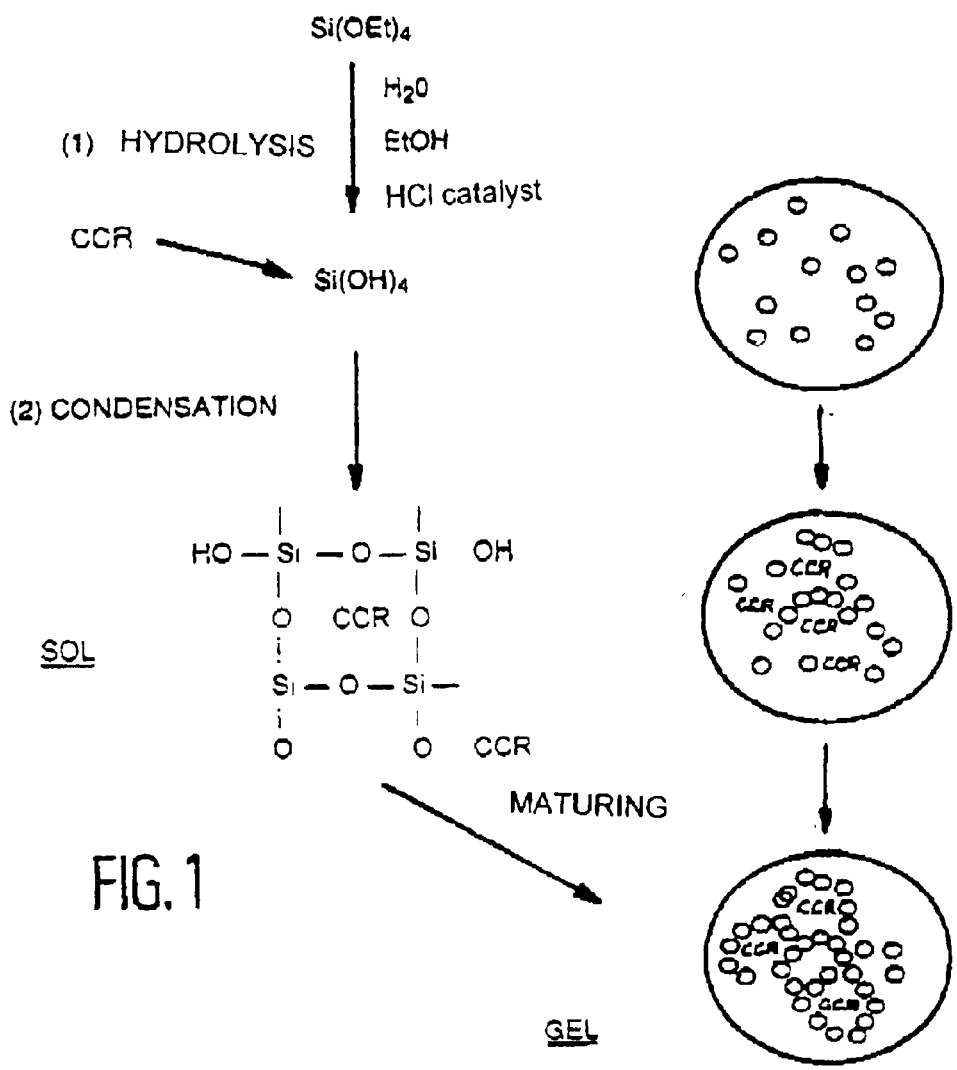
FIG. 1 is a schematic illustration of the sol-gel method used for the invention.

FIG. 1 shows a sol-gel method for producing a silica-based porous film containing a coloured indicator formed of Chromoxane Cyanine R (CCR).

As illustrated in this figure, the starting alcoxysilane is tetraethoxysilane $Si(OEt)_4$ in solution in ethanol EtOH, to which is added water $H_2O$ and an acid catalyst, hydrochloric acid HCl, and a coloured indicator CCR.

Hydrolysis leads to $Si(OH)_4$ which, by condensation, gives a sol in which the CCR molecules are trapped. By sol maturing, a gel is obtained as shown in this figure. Generally, the sol-gel matrix is prepared at room temperature in a clean environment protected from draughts and, if possible, under controlled temperature and hygrometry.

To implement the method of the invention, an optic fibre such as a silica fibre may be used comprising an optic sheath in hard polymer and an outer sheath in Tefzel, having a total length of 256 mm. The central part of this fibre, or active part, is uncovered, over 100 mm for example, to expose the core of the fibre. It is possible to conduct a first mechanical removing operation to remove the outer Tefzel sheath, and a second removal operation under heat to remove the optic sheath of hard polymer. Sol-gel depositing is then carried out on the active part of this fibre previously cleaned with ethanol for example.

This depositing may be made by placing the fibre vertically in a tube containing the sol, then by withdrawing it vertically at a slow, constant rate, for example at 1 mm/s. The ends of the mechanical sheath immersed in the sol-gel solution are then cleaned with alcohol. After depositing, the coated fibre is dried, for example at a temperature of 100° C., so that the film adheres to the fibre and porosity is reduced.

This depositing step is conducted away from any draughts of air to obtain a uniform deposit thickness when the solvent is evaporated It is also possible to conduct several successive deposits by immersing the fibre in the sol to obtain the desired thickness.

The following examples illustrate the preparation of the sensors using the method of the invention.

EXAMPLE 1

Sensors 1 and 2 are prepared from two identical sols, obtained by successively adding to a sealed flask in opaque glass: absolute ethanol, 99% pure tetraethoxysilane (TEOS), dilute hydrochloric acid and the coloured indicator CCR having a molecular weight M of 536.4 and 40% purity.

For this preparation, the quantity of hydrochloric acid used is such that the pH of the aqueous phase of the sol is 0.72, the water/TEOS molar ratio is 6, the ethanol/TEOS molar ratio is 10 and CCR concentration represents 1 mole CCR per 335 moles TEOS.

The mixture is homogenized for 1 hour at room temperature, and it is then placed in sealed storage in an oven at 55° C. for a maturing time of 50 hours, before the sol is deposited on the fibre using the above-described method.

After depositing the film, vacuum drying is conducted at 100° C. for 24 hours and the sensor is then stored for 3 weeks in ambient atmosphere.

EXAMPLE 2

The same operating mode is followed as in example 1 to prepare sensors 3 to 8, using the same parameters for the method except those concerning the pH of the aqueous phase of the sol and temperature.

Table 1 below illustrates the values chosen for the pH of the aqueous phase and maturing temperature to prepare sensors 1 to 8.

TABLE 1

| Sensor | pH | Temperature (° C.) |
|--------|------|--------------------|
| 1 | 0.72 | 55 |
| 2 | 0.72 | 55 |
| 3 | 0.44 | 42 |
| 4 | 0.44 | 68 |
| 5 | 0.99 | 42 |
| 6 | 1.27 | 55 |
| 7 | 0.17 | 55 |
| 8 | 0.99 | 68 |

Sensors 1 to 4 prepared as described above, have the following characteristics:

The thickness of the film is in the region of 100 nm for a sol layer deposit. This thickness is measured on optic fibre by scanning electronic microscopy (SEM) and on silicon plate by X reflectometry and ellipsometry.

The density of the film is 1.85 g.cm$^{-3}$ measured by X reflectometry. The deduced porous volume is 16%.

The refractive index of the film is 1.44 compared with 1.46 for the index of the optic fibre core in melted silica. This value was obtained by ellipsometry on silicon plate.

The chemical sensors thus obtained were tested in 8 N nitric medium.

For this purpose, the device shown in FIG. 2 is used.

This device comprises an xenon lamp 1 which sends a light beam onto sensor 3 in contact with the medium to be measured and onto a reference line 5 measuring possible fluctuations in the lamp signal. The light beams are then directed by optic fibres 7 into a plane field spectrophotometer 9 fitted with mirrors and a Charge Coupled Device detector (CCD) which is a two-dimension matrix detection system, the columns representing wavelengths and the lines representing the position of the 10 fibres (or 10 measurement channels) as seen by the detector.

The absorption spectra of the sensor in 1N $HNO_3$ medium are obtained which is the reference, and the spectra corresponding to the sensors in 8 N $HNO_3$ medium, i.e. the measurement. The optic density is determined on these absorption spectra at the wavelength of maximum absorption located at 545 nanometres, compared with the reference which is 1 N nitric acid.

Figure 3:
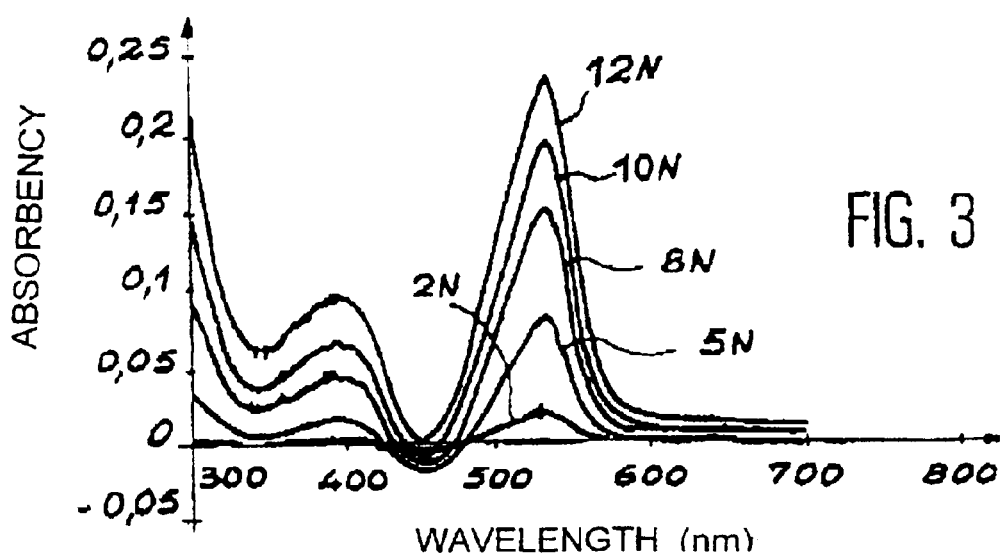
FIG. 3 shows the absorption spectra of a sensor conforming to the invention, in a pure nitric medium, for acidity values ranging from 2 to 10 N relative to a 1 N reference.

FIG. 3 shows the absorption spectra obtained for nitric acid concentrations of 2, 5, 8, 10 and 12 N.

The stability of the signal emitted by each of sensors 1 to 8 in a nitric medium is verified by measuring the optic density at time $t_o$, which is 0.14 for 8 N $HNO_3$ and which corresponds to 100% of the signal; then the optic signal is determined in relation to time by its expression as a percentage of initial optic density, measured for the concentration $HNO_3$=8 N.

Figure 4:
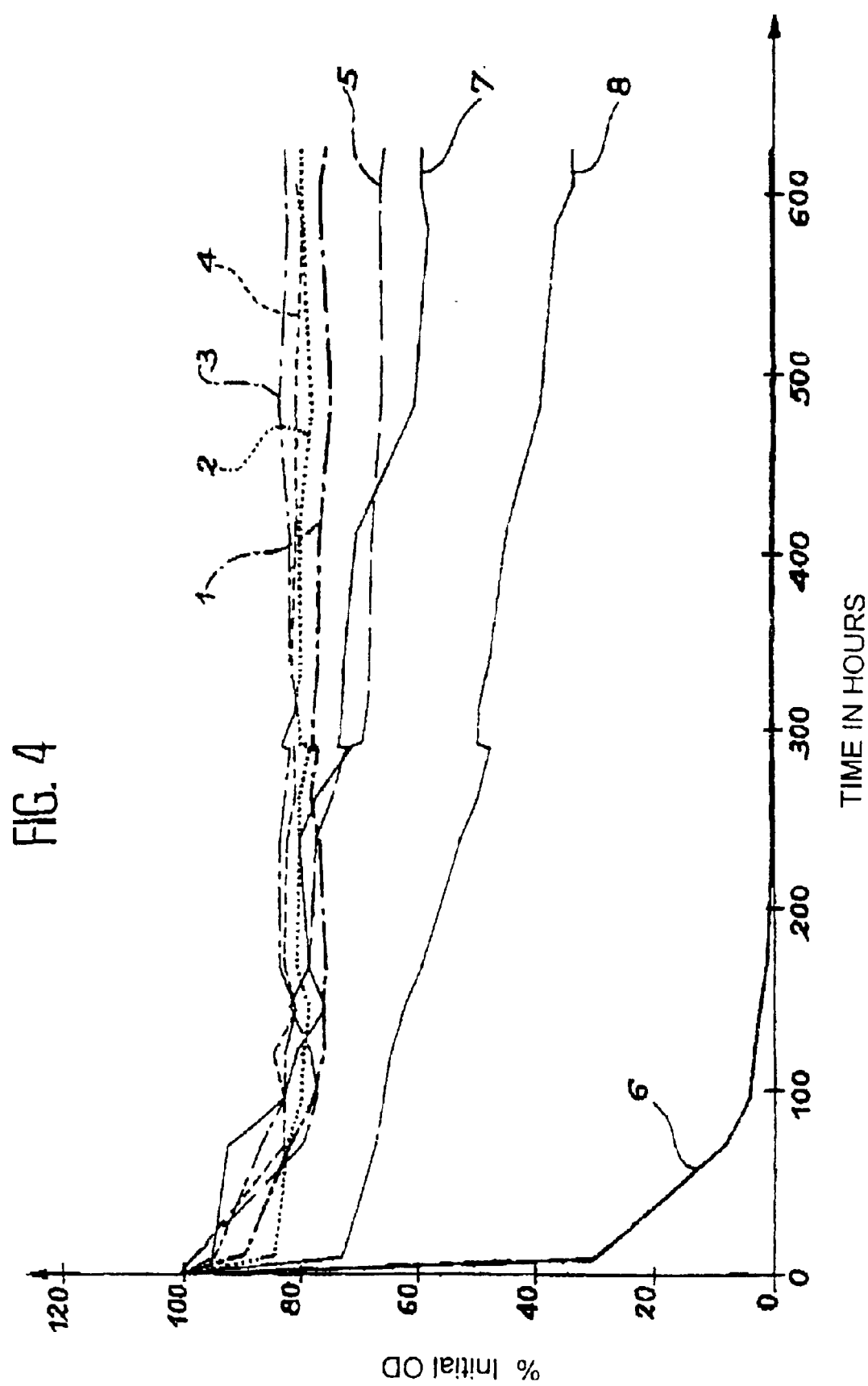
FIG. 4 illustrates changes in the signal transmitted by different sensors in relation to time in hours, curves 1 to 4 relate to sensors conforming to the invention, whereas curves 5 to 8 are given by way of comparison and represent sensors which do not conform to the invention.

The results obtained are shown in FIG. 4 which illustrates the changes in the signals emitted by sensors 1 to 8 in relation to time (in hours).

In this figure, it can be seen that the best results are obtained with sensors 1 to 4 produced with a pH of 0.72 or less, and that sensors 5 and 7 also correspond to average stability.

On the other hand, sensors 6 and 8 show no signal stability.

Therefore, it is verified that the choice of parameters such as pH, temperature and maturing time, according to the invention, play a very important role in results, in particular in respect of sensor stability.

The response of the sensors of the invention was also measured in the presence of metallic cations such as $FE^{3+}$, $Ce^{3+}$, $UO_2^{2+}$, Pu (IV), U (IV) and it was verified that for contents of these elements lower than 10 g.$L^{-1}$, comparable results were obtained.

Cited References

[1] M. H. Noiré et al, Sensors and Actuators B51, 1998, pages 214–219.

[2] M. H. Noiré et al, Journal of Sol-Gel Sciences and Technology 17, 2000 pages 131–136.

What is claimed is:

1. Method for producing a silica-based optic fibre chemical sensor which can be used to analyse a chemical species present in a liquid or gas, consisting of chemically grafting onto the core of the optic fibre a porous film containing a coloured indicator sensitive to the chemical spedies to be analysed, by conducting the following steps:
   a) preparing a sol by acid-catalysed hydrolysis of a solution of an alcoxysilane in an alcohol containing the coloured indicator,
   b) maturing to sol,
   c) depositing the sol on the core of the optic fibre, and
   d) drying
   characterized in that in step a), the quantity of acid used is such that the pH of the aqueous phase of the sol lies between 0.44 and 0.72.

2. Method according to claim 1, in which for step b) the sol is matured at a temperature of 40 to 70° C. for a time of no more than three days.

3. Method according to claim 2, in which the maturing temperature is 50 to 60° C.

4. Method according to claim 2, in which the sol maturing time is from 24 to 50 hours.

5. Method according to claim 1, in which the hydrolysis in step a) is conducted using a water:alcoxysilane molar ratio of 4 to 6.

6. Method according to claim 1, in which for step d) drying is conducted in a vacuum for 20 to 30 hours.

7. Method according to claim 6, in which the drying time is approximately 24 hours.

8. Method according to claim 1, in which the sensor is also stored for at least three weeks before use.

9. Method according to claim 1, in which for step a) a solution of tetraethoxysilane in ethanol is used having an ethanol:tetraethoxysilane molar ratio of approximately 10.

10. Method according to claim 5, in which for step a) a solution of tetraethoxysilane in ethanol is used having an ethanol:tetraethoxysilane molar ratio of approximately 10.

11. Method according to claim 1, in which the coloured indicator/alcoxysilane molar ratio is 1:335.

12. Method according to claim 1, in which the species to be analysed is nitric acid in the concentration range of 1 to 10 $mol.L^{-1}$.

13. Method according to claim 12, in which the coloured indicator is Chromoxane Cyanine R.

14. Method according to claim 12, in which the coloured indicator is Chromazurol S.

15. Method according to claim 1, in which the species to be analysed is nitric acid in the concentration range of 0.1 to 2 $mol.L^{-1}$.

16. Method according to claim 15, in which the coloured indicator is chosen from among Thymol Blue, Phenol Red and Pyrocatechol Violet.

* * * * *